United States Patent [19]

Lagrange et al.

[11] Patent Number: 5,556,989

[45] Date of Patent: Sep. 17, 1996

[54] INDOLINE COMPOUNDS USEFUL FOR DYEING KERATINOUS FIBRES

[75] Inventors: Alain Lagrange, Coupvray; Jean J. Vandenbosche, Sevran; Hervé Andrean, Paris, all of France

[73] Assignee: L'Oreal, Paris, France

[21] Appl. No.: 401,671

[22] Filed: Mar. 10, 1995

Related U.S. Application Data

[62] Division of Ser. No. 165,853, Dec. 14, 1993, Pat. No. 5,427,588.

[30] Foreign Application Priority Data

Dec. 18, 1992 [FR] France ................................ 92 15675

[51] Int. Cl.⁶ ............................................... C07D 209/08
[52] U.S. Cl. ................................................ 548/491
[58] Field of Search ..................................... 548/491

[56] References Cited

U.S. PATENT DOCUMENTS

| | | |
|---|---|---|
| 4,428,881 | 1/1984 | Hedrich et al. |
| 5,182,403 | 1/1993 | Brickner ............................ 548/231 |

FOREIGN PATENT DOCUMENTS

| | | |
|---|---|---|
| 0247266 | 12/1987 | European Pat. Off. |
| 0462857 | 12/1991 | European Pat. Off. |
| 0530629 | 3/1993 | European Pat. Off. |
| 2008797 | 1/1970 | France. |
| 2681318 | 3/1993 | France. |
| 9217157 | 10/1992 | WIPO. |

OTHER PUBLICATIONS

Mazza et al, "N–acylindolines with phytotoxic activity"; Chemical Abstracts vol. 86, 1977, Abstract No. 13972n.

Primary Examiner—Jacqueline Haley
Attorney, Agent, or Firm—Cushman Darby & Cushman, L.L.P.

[57] ABSTRACT

The invention relates to indoline compounds of formula (I):

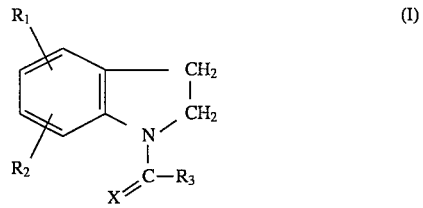

in which:

$R_1$ and $R_2$ denote hydrogen, alkyl, monohydroxyalkyl, polyhydroxyalkyl, nitro, hydroxyl, alkoxy or NHR where R can be hydrogen, alkyl, monohydroxyalkyl or polyhydroxyalkyl;

X denotes oxygen or sulfur;

$R_3$ represents $-OR_4$ or $NR_5R_6$ where $R_4$ denotes alkyl, alkenyl, benzyl, alkoxyalkyl or haloalkyl;

$R_5$ and $R_6$ denote alkyl;

$R_1$ and $R_2$ not simultaneously denoting hydrogen or nitro and when $R_1$ denotes alkyl, alkoxy or mono- or polyhydroxyalkyl, $R_2$ denotes NHR or hydroxyl, and to their use in dyeing keratinous fibers.

2 Claims, No Drawings

INDOLINE COMPOUNDS USEFUL FOR DYEING KERATINOUS FIBRES

This is a division of application Ser. No. 08/165,853, filed Dec. 14, 1993 now U.S. Pat. No. 5,427,588.

The present invention relates to new indoline compounds and to their use in dyeing keratinous fibers, in particular human keratinous fibers such as hair, to the dyeing compositions and to the dyeing processes using these indolines.

It was already proposed in the past to dye hair by using, as couplers, certain monohydroxyindolines or monoaminoindolines, in particular in French Patent No. 2,008,797; U.S. Pat. No. 4,013,404 describes mono- or diaminoindolines or monohydroxyindolines as oxidation base or as couplers, used in oxidation dyeing of hair.

The Applicant has discovered new compounds of indoline type which can be used for dyeing keratinous fibers, in particular hair.

The subject of the invention is thus the use for dyeing keratinous fibers, in particular hair, of new indolines and of their salts of formula (I) defined below.

Another subject of the invention consists of the dyeing compositions intended for dyeing keratinous fibers and in particular human hair containing at least one indoline of formula (I) defined below.

Another subject of the invention is the dyeing processes using these compounds.

Other subjects of the invention will become apparent on reading the description and examples which follow.

The new indolines used for dyeing keratinous fibers and in particular human keratinous fibers such as hair, in accordance with the invention, are essentially characterized in that they correspond to the formula:

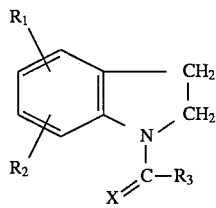

(I)

in which:

$R_1$ and $R_2$, independently of one another, represent a hydrogen atom or a $C_1$–$C_4$ alkyl, $C_1$–$C_4$ monohydroxyalkyl, $C_2$–$C_4$ polyhydroxyalkyl, nitro, hydroxyl, $C_1$–$C_4$ alkoxy or NHR group, it being possible for R to represent a hydrogen atom or a $C_1$–$C_4$ alkyl, $C_1$–$C_4$ monohydroxyalkyl or $C_2$–$C_4$ polyhydroxyalkyl group;

X represents an oxygen atom or a sulfur atom;

$R_3$ represents the —$OR_4$ or $NR_5R_6$ groups, in which:

$R_4$ represents a linear or branched $C_1$–$C_{10}$ alkyl, linear or branched $C_2$–$C_{10}$ alkenyl, benzyl, alkoxyalkyl (the alkyl and alkoxy groups having from 1 to 4 carbon atoms) or $C_1$–$C_4$ haloalkyl radical;

$R_5$ and $R_6$, independently of one another, represent a $C_1$–$C_4$ alkyl;

with the proviso that $R_1$ and $R_2$ cannot simultaneously denote a hydrogen atom or a nitro group and that when $R_1$ denotes an alkyl, alkoxy or mono- or polyhydroxyalkyl radical, $R_2$ represents a hydroxyl or NHR radical, R having the meanings shown above; with the exception of the compounds 6-nitro-1-(N,N-dimethylcarbamoyl)indoline and 5-amino-1-(N,N-dimethylcarbamoyl)indoline.

Mention may be made, among the compounds corresponding to the formula (I), of:

(1) 5,6-dihydroxy-1-(benzyloxycarbonyl)indoline,
(2) 5,6-dihydroxy-1-(ethyloxycarbonyl)indoline,
(3) 5,6-dihydroxy-1-(isopropyloxycarbonyl)indoline,
(4) 5,6-dihydroxy-1-(allyloxycarbonyl)indoline,
(5) 5,6-dihydroxy-1-(2,2,2-trichloroethoxycarbonyl)indoline,
(6) 5,6-dihydroxy-1-(2-ethylhexyloxycarbonyl)indoline,
(7) 5,6-dihydroxy-1-(methoxyethoxycarbonyl)indoline,
(8) 5,6-dihydroxy-1-(dimethylcarbamoyl)indoline,
(9) 4-hydroxy-5-methoxy-1-(benzyloxycarbonyl)indoline,
(10) 6-hydroxy-7-methoxy-1-(benzyloxycarbonyl)indoline,
(11) 5,6-dihydroxy-1-(ethylthiocarbonyl)indoline,
(12) 5-methoxy-6-hydroxy-1-(benzyloxycarbonyl)indoline.

Among these compounds, Compounds (1), (4), (5), (9), (10) and (12) are preferred.

The compounds of formula (I) are prepared according to a conventional synthetic process which consists in preparing, with stirring, a suspension of indoline hydrobromide of formula:

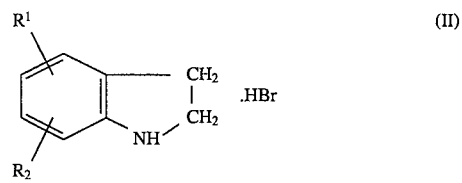

(II)

in which $R_1$ and $R_2$ have the same meanings as in the formula (I), and which contains calcium carbonate and dioxane.

A chloroformate or chloroformamide corresponding to the carbamate or amide which it is desired to obtain is added at room temperature.

Stirring is continued. After a few minutes, the reaction being exothermic, the temperature of the mixture reaches 40°/45° C. Stirring is continued for a further additional 5 to 20 minutes.

The suspension is then poured onto ice. A precipitate is then formed which is acidified with hydrochloric acid. The precipitate is then filtered off and then washed successively with water, ethanol, isopropyl ether and finally petroleum ether. Once dried, the precipitate is recrystallized from acetic acid or ethanol.

The indolines of formula (I) defined above are generally used with the aid of compositions which constitute another subject of the invention.

The dyeing compositions intended to be used for dyeing keratinous fibers and in particular human keratinous fibers such as hair, in accordance with the invention, are characterized in that they contain, in a medium suitable for dyeing, at least one indoline corresponding to the formula (I) defined above.

The amount of indoline of formula (I) used in the composition is generally in proportions from 0.01 to 8% by weight with respect to the total weight of the composition and preferably from 0.03 to 5% by weight.

These compositions can be provided in various forms, especially in the form of more or less thickened lotions, of creams, of foams and of gels, optionally packaged in aerosol form.

They can also constitute an ingredient of a multi-component dyeing agent laid out in a multi-compartment device or dyeing kit.

The medium suitable for dyeing is preferably an aqueous medium which must be cosmetically acceptable when the compositions are intended to be used for dyeing living human hair. This aqueous medium can consist of water or a water/solvent(s) mixture.

The pH of the compositions is between 4 and 12.

The solvents are chosen from organic solvents and preferentially from dimethyl isosorbide, $C_2$–$C_4$ alcohols, ethylene glycol, the monomethyl, monoethyl and monobutyl ethers of ethylene glycol, the acetate of the monoethyl ether of ethylene glycol, propylene glycol, the monomethyl ethers of propylene glycol and of dipropylene glycol, or methyl lactate.

A particularly preferred solvent is the water/dimethyl isosorbide mixture.

When the medium suitable for dyeing consists of a water/solvent(s) mixture, the solvents are used in concentrations between 0.5 and 75% by weight with respect to the total weight of the composition.

The compositions in accordance with the invention can contain adjuvants commonly used for dyeing keratinous fibers and in particular cosmetically acceptable adjuvants when these compositions are applied to dyeing living human hair.

These compositions can especially contain fatty amides in preferential proportions of 0.05 to 10% by weight, anionic, cationic, nonionic or amphoteric surface-active agents or their mixtures, preferably present in proportions between 0.1 and 50% by weight, thickening agents, fragrances, sequestering agents, film-forming agents, treatment agents, dispersing agents, conditioning agents, preserving agents, opacifying agents, or agents for swelling keratinous fibers.

The thickening agents are preferably chosen from sodium alginate, gum arabic, guar gum, heterobiopolysaccharides such as xanthangum, scleroglucans, cellulose derivatives such as methyl cellulose, hydroxyethyl cellulose, hydroxypropyl methyl cellulose or the sodium salt of carboxymethyl cellulose, and crosslinked acrylic acid polymers.

It is also possible to use inorganic thickening agents, such as bentonite.

These thickeners are used alone or as a mixture and are preferably present in proportions between 0.1 and 5% by weight with respect to the total weight of the composition and advantageously between 0.5 and 3% by weight.

The basifying agents which can be used in the compositions can be in particular amines, such as alkanolamines or alkylamines, or alkali metal or ammonium hydroxides or carbonates.

The acidifying agents which can be used in these compositions can be chosen from lactic acid, acetic acid, tartaric acid, phosphoric acid, hydrochloric acid or citric acid.

Of course, it is possible to use any other cosmetically acceptable, especially in the case of dyeing hair, basifying or acidifying agent.

When the compositions are used in the foam form, they can be packaged under pressure and in an aerosol container in the presence of a propellant and of at least one foam generator.

The foam-generating agents can be anionic, cationic, nonionic or amphoteric foaming polymers or their mixtures or surface-active agents of the type of those defined above.

The process for dyeing keratinous fibers, in particular human keratinous fibers, which constitutes another subject of the invention is essentially characterized in that it consists in applying to these fibers a composition (A) defined above and containing, in a medium suitable for dyeing, at least one indoline of formula (I) defined above, in maintaining the composition in contact with the fibers for a time sufficient to develop the coloring, with the aid of an oxidizing system, in rinsing and optionally in washing the fibers thus dyed.

According to the invention, the color is developed using a chemical oxidizing system chosen from:

(i) iodide ions and hydrogen peroxide, the composition (A) containing the indoline of formula (I) additionally comprising in this case either iodide ions or hydrogen peroxide, and the application of the composition (A) is preceded or followed by the application of a composition (B) which contains, in a medium suitable for dyeing, either:
  (a) hydrogen peroxide at a pH between 2 and 12 and preferably between 2 and 7, when the composition (A) contains iodide ions, or
  (b) iodide ions at a pH between 3 and 11, when the composition (A) contains hydrogen peroxide;

(ii) nitrites, the application of the composition (A) containing the indoline of formula (I) being followed by the application of an aqueous composition (B) having an acidic pH, the composition (A) or the composition (B) containing at least one nitrite;

(iii) oxidizing agents chosen from hydrogen peroxide, periodic acid and its water-soluble salts, sodium metaperiodate, sodium hypochlorite, chloramine-T, chloramine-B, potassium ferricyanide, silver oxide, Fenton's reagent, lead(IV) oxide, cesium sulfate, ammonium persulfate, or alkali metal chlorites; these oxidizing agents being present in the composition (A) containing the indoline of formula (I) or applied simultaneously or sequentially by means of a composition (B) containing them in a medium suitable for dyeing;

(iv) anions of a metal chosen from permanganates or dichromates, these oxidizing agents being applied by means of an aqueous composition (B), at a pH of 2 to 10, before the application of the composition (A);

(v) metal salts of groups 3 to 8 of the periodic table, these metal salts being applied by means of a composition (B) containing them in a medium suitable for dyeing, the composition (B) being applied prior to or subsequent to the application of the composition (A);

(vi) rare-earth metal salts, these rare-earth metal salts being applied by means of a composition (B) containing them in a medium suitable for dyeing, the composition (B) being applied prior to or subsequent to the application of the composition (A) containing the indoline of formula (I);

(vii) a quinone derivative chosen from ortho- or parabenzoquinones, monoimines or diimines of ortho- or parabenzoquinones, 1,2- or 1,4-naphthoquinones, sulfonimides of ortho- or parabenzoquinones, $\alpha,\omega$-alkylenebis- 1,4-benzoquinones, or monoimines or diimines of 1,2- or 1,4-naphthoquinones, the indoline of formula (I) and the quinone derivatives being chosen so that the difference in oxidation-reduction potential AE between the oxidation-reduction potential Ei of the indoline of formula (I), determined at pH 7 in phosphate medium on a vitreous carbon electrode by voltametry, and the oxidation-reduction potential Eq of the quinone derivative, determined at pH 7 in phosphate medium by polarography on a mercury electrode with reference to the saturated calomel electrode, is such that:

$$\Delta E = Ei - Eq \leq 320 \text{ millivolts.}$$

According to a preferred form of the invention, the application of the compositions (A) and (B) is separated by a rinsing-with-water stage.

According to a first variant of the dyeing process using oxidizing systems, there is applied to the keratinous matter a composition (A) containing, in a medium suitable for dyeing, at least one compound of formula (I) in combination with iodide ions, the application of the composition (A) being preceded or followed by the application of a composition (B) which contains, in a medium suitable for dyeing, hydrogen peroxide.

This process can also be used by applying to keratinous fibers at least one composition (A) containing, in a medium suitable for dyeing, the compound of formula (I) in combination with hydrogen peroxide, having a pH between 2 and 7, and preferably between 3.5 and 7, the application of the composition (A) being preceded or followed by the application of a composition (B) which contains, in a medium suitable for dyeing, iodide ions.

The iodide ion in this variant of the process is preferably chosen from alkali metal, alkaline-earth metal or ammonium iodides. The iodide more particularly consists of potassium iodide.

The iodide ions are present in the compositions (A) or (B) in proportions generally between 0.007 and 4% by weight, expressed as $I^-$ ions, and preferably between 0.08 and 1.5% by weight with respect to the total weight of the composition (A) or (B).

According to a second variant, this process can be implemented by using a nitrite as oxidizing agent for developing the coloring. The nitrites which can more particularly be used in accordance with the invention are:

alkali metal, alkaline-earth metal or ammonium nitrites or nitrites of any other cosmetically acceptable cation when it is used for dyeing living human hair;

organic nitrite derivatives such as, for example, amyl nitrite;

nitrite carriers, that is to say compounds which, by conversion, form nitrites of the type defined above.

The particularly preferred nitrites are sodium, potassium or ammonium nitrite.

This variant of the process is implemented by applying to the keratinous matter the composition (A) based on the compound of formula (I) defined above and then that of an acidic aqueous composition (B), the composition (A) or (B) containing at least one nitrite.

The nitrites are generally used in proportions between 0.02 and 1 mol/liter.

According to a third variant of this process, the oxidizing agents are chosen from hydrogen peroxide, chloramine-T, chloramine-B, periodic acid and its water-soluble salts, sodium metaperiodate, sodium hypochlorite, potassium ferricyanide, silver oxide, Fenton's reagent, lead(IV) oxide, cesium sulfate or ammonium persulfate. These agents are preferably applied to the fibers by means of a composition (B) and after the application of the composition (A).

These oxidizing agents are present in proportions sufficient to develop a coloring and preferably in proportions between 0.004 mol and 0.7 mol, in particular between 0.01 mol and 0.04 mol, per 100 g of composition.

According to this third variant, sodium metaperiodate is particularly preferred.

According to a fourth variant of this process, there is applied to the keratinous fibers, in a first step, a composition containing, in a medium suitable for dyeing, at a pH between 2 and 10, an anion of a metal having good affinity for keratin having an oxidation-reduction potential greater than that of the compounds of formula (I). This anion is preferably chosen from permanganates or dichromates and more particularly potassium permanganate and sodium dichromate.

These metal anions are generally used at anion molalities greater than $10^{-3}$ mol/1000 g up to preferably 1 mol/1000 g.

In a second step, there is applied a composition containing, in a medium suitable for dyeing, at a pH between 4 and 10, a compound corresponding to the formula (I) defined above.

The compositions containing anions must not contain organic agents having a reducing effect on anions.

According to a fifth variant of the invention, oxidation catalysts chosen from metal salts, such as manganese, cobalt, iron, copper and silver salts, are used.

By way of example, it is possible to use manganese sulfate, manganese lactate, cobalt chloride, ferric chloride, cupric chloride, ammoniacal silver nitrate or copper sulfate.

The preferred salts are copper salts. These salts are used in proportions from 0.01 to 2%, expressed as metal ions, with respect to the total weight of the composition used and containing these salts.

According to this variant, keratinous fibers, in particular hair, are brought into contact with a composition (B) containing, in a medium suitable for dyeing, the metal salt, before or after the application of the composition (A) containing the compound of formula (I), and rinsing is preferably carried out between the two stages.

The preferred implementation consists in applying a cupric salt in a first step and the composition (A) containing the indoline of formula (I) in a second step.

According to this variant, copper sulfate is particularly preferred.

This dyeing can be followed, after rinsing, by the application of a hydrogen peroxide solution.

According to a sixth variant, rare-earth metal salts are used. The rare-earth metal salts which can be used in accordance with the invention are chosen from lanthanide salts and especially cerium $Ce^{3+}$, $Ce^{4+}$, lanthanum $La^{3+}$, europium $Eu^{2+}$, $Eu^{3+}$, gadolinium $Gd^{3+}$, ytterbium $Yb^{2+}$, $Yb^{3+}$ or dysprosium $Dy^{3+}$ salts. The preferred salts are in particular sulfates, chlorides or nitrates.

These rare-earth metal salts are present in proportions between 0.1 and 8% by weight with respect to the total weight of the composition.

Cerium $Ce^{3+}$, $Ce^{4+}$ salts, in the sulfate and chloride form, are preferably used.

According to a seventh variant, the composition containing the quinone derivative is applied before or after the composition (A) containing the compound of formula (I).

By way of example of quinone derivative, mention may be made of 1,4-benzoquinone and 2-hydroxyethylthio-1,4-benzoquinone.

The concentration of quinone derivatives is preferably between 0.005 and 1 mol/liter in the composition (B). The pH of the composition (B) is between 2 and 10 and preferably less than 7.

When compositions based on hydrogen peroxide are used in the various processes described above, the hydrogen peroxide content is generally between 1 and 40 volumes and preferably between 2 and 10 volumes and more particularly between 3 and 10 volumes.

Another subject of the invention is a multi-component agent for coloring keratinous fibers, and in particular human keratinous fibers, intended especially to be used in the implementation of the dyeing process defined above and using an oxidizing system. In this case, the dyeing agent comprises at least two components, the first of which consists of the composition (A) defined above and containing the indoline of formula (I) and the other component consists of one of the compositions (B) also defined above.

The respective components (A) and (B) are chosen according to the different variants of the process explained above.

Another subject of the invention is a multi-compartment device or also "dyeing kit" or "dyeing pack" containing all the components intended to be applied in the one dyeing to keratinous fibers in single or successive applications, with or without premixing as mentioned above.

Such devices are known in themselves and can comprise a first compartment containing the composition (A) containing the indoline of formula (I) in a medium suitable for dyeing and, in a second compartment, a composition (B) of the type defined above and containing the oxidizing agent.

The multi-compartment devices which can be used in accordance with the invention can be equipped with means for mixing at the time of use and their contents can be packaged under an inert atmosphere.

When the medium containing the indoline of formula (I) is anhydrous, a third compartment may be provided containing an aqueous medium suitable for dyeing and intended to be mixed, immediately before use, with the composition of the first compartment.

The indoline of formula (I), the compositions and the process in accordance with the invention can be used for dyeing straightened or unstraightened, permanent wave or nonpermanent wave, natural or already dyed hair or strongly or slightly bleached, optionally permanent wave, hair.

It is also possible to use them for dyeing fur or wool.

The examples are intended to illustrate the invention without, however, any limiting nature being implied.

PREPARATION EXAMPLES

EXAMPLE 1

Preparation of
5,6-dihydroxy-1-(benzyloxycarbonyl)indoline

A suspension of 5,6-dihydroxyindoline hydrobromide (69.6 g, 0.3M) and calcium carbonate (0.6M, i.e. 60 g) in 345 ml of dioxane is prepared. 90 ml of water are added and the mixture stirred for 3 minutes. 56.1 g (0.33M) of benzyl chloroformate are then added in a single step at room temperature and while still stirring. Stirring is maintained for approximately 20 minutes. The reaction is exothermic (40°/45° C.). The suspension is then poured onto ice. A white precipitate is formed which is acidified with hydrochloric acid and then filtered off and washed successively with water, ethanol, isopropyl ether and petroleum ether. The precipitate is dried and recrystallized from ethanol.

White crystals of the expected product are obtained with a yield of 79%, the product having the following elemental analysis:

|  | C | H | N | O |
|---|---|---|---|---|
| Calculated | 67.36 | 5.30 | 4.91 | 22.43 |
| Found | 67.33 | 5.25 | 5.02 | 22.55 |

EXAMPLE 2

Preparation of
5,6-dihydroxy-1-(ethyloxycarbonyl)indoline

A suspension of 5,6-dihydroxyindoline hydrobromide (34.8 g, 0.15M) and calcium carbonate (30 g, 0.3M) in 120 ml of dioxane is prepared. 10 ml of water are added and the mixture is stirred for 3 minutes. The reaction is then carried out as in Example 1, except that 15.9 g (0.165M) of ethyl chloroformate are added.

White crystals of the expected product are obtained with a yield of 81%, the product having the following elemental analysis:

|  | C | H | N | O |
|---|---|---|---|---|
| Calculated | 59.19 | 5.87 | 6.27 | 28.67 |
| Found | 59.06 | 5.88 | 6.21 | 28.95 |

EXAMPLE 3

Preparation of
5,6-dihydroxy-1-(isopropyloxycarbonyl)indoline

The reaction is carried out as in Example 2, except that 21.3 g (0.165M) of isopropyl chloroformate are used.

White crystals of the expected product are obtained with a yield of 67%, the product having the following elemental analysis:

|  | C | H | N | O |
|---|---|---|---|---|
| Calculated | 62.14 | 6.82 | 5.57 | 25.47 |
| Found | 62.08 | 6.85 | 5.53 | 25.58 |

EXAMPLE 4

Preparation of
5,6-dihydroxy-1-(allyloxycarbonyl)indoline

The reaction is carried out as in Example 2, except that 17.4 g (0.165M) of allyl chloroformate are used.

White crystals of the expected product are obtained with a yield of 88%, the product having the following elemental analysis:

|  | C | H | N | O |
|---|---|---|---|---|
| Calculated | 61.27 | 5.57 | 5.95 | 27.21 |
| Found | 61.11 | 5.61 | 5.86 | 27.27 |

EXAMPLE 5

Preparation of
5,6-dihydroxy-1-(2,2,2-trichloroethoxycarbonyl)indoline

The reaction is carried out as in Example 2, except that 35 g (0.165M) of 2,2,2-trichloroethyl chloroformate are used.

White crystals of the expected product are obtained with a yield of 75%, the product having the following elemental analysis:

|  | C | H | N | O | Cl |
|---|---|---|---|---|---|
| Calculated | 40.46 | 3.09 | 4.29 | 19.60 | 32.57 |
| Found | 40.52 | 3.07 | 4.05 | 19.61 | 32.44 |

EXAMPLE 6

Preparation of 5,6-dihydroxy-1-(2-ethylhexyloxycarbonyl)indoline

The reaction is carried out as shown in Example 2, except that 31.8 g (0.165M) of 2-ethylhexyl chloroformate are used.

White crystals of the expected product are obtained with a yield of 40%, the product having the following elemental analysis:

|            | C     | H    | N    | O     |
|------------|-------|------|------|-------|
| Calculated | 66.43 | 8.18 | 4.56 | 20.82 |
| Found      | 66.51 | 8.18 | 4.52 | 20.71 |

EXAMPLE 7

Preparation of 5,6-dihydroxy-1-(methoxyethoxycarbonyl)indoline

The reaction is carried out as shown in Example 2, except that 24.9 g (0.18M) of methoxyethyl chloroformate are used.

White crystals of the expected product are obtained with a yield of 80%, the product having the following elemental analysis:

|            | C     | H    | N    | O     |
|------------|-------|------|------|-------|
| Calculated | 56.91 | 5.97 | 5.53 | 31.59 |
| Found      | 56.86 | 6.09 | 5.45 | 31.53 |

EXAMPLE 8

Preparation of 5,6-dihydroxy-1-(dimethylcarbamoyl)indoline

The reaction is carried out as shown in Example 1, except that there are used:

46.4 g (0.2M) of 5,6-dihydroxyindoline, 40 g (0.4M) of calcium carbonate, 300 ml of dioxane, 60 ml of water, 38.7 g (0.36M) of dimethylcarbamoyl chloride.

White crystals of the expected product are obtained with a yield of 16%, the product having the following elemental analysis:

|            | C     | H    | N     | O     |
|------------|-------|------|-------|-------|
| Calculated | 59.46 | 6.35 | 12.60 | 21.60 |
| Found      | 58.88 | 6.52 | 12.32 | 22.32 |

EXAMPLE 9

Preparation of 4-hydroxy-5-methoxy-1-(benzyloxycarbonyl)indoline

The reaction is carried out as shown in Example 1, except that there are used:

30.2 g (0.15M) of 4-hydroxy-5-methoxyindoline, 15.0 g (0.15M) of calcium carbonate, 130 ml of dioxane, 12 ml of water, 12.5 ml (0.15M) of aqueous ammonia (which are added at the same time as the water), 24.0 g (0.17M) of benzyl chloroformate.

White crystals of the expected product, crystallized with ¼ $H_2O$, are obtained with a yield of 85%, the product having the following elemental analysis:

|            | C     | H    | N    | O     |
|------------|-------|------|------|-------|
| Calculated | 67.22 | 5.76 | 4.61 | 22.40 |
| Found      | 67.26 | 6.03 | 4.38 | 22.55 |

EXAMPLE 10

Preparation of 6-hydroxy-7-methoxy-1-(benzyloxycarbonyl)indoline

The reaction is carried out as shown in Example 9, except that there are used:

16.1 g (0.08M) of 6-hydroxy-7-methoxyindoline, 8.0 g (0.08M) of calcium carbonate, 64 ml of dioxane, 6 ml of water, 6 ml of aqueous ammonia (0.08M), 15 g (0.088M) of benzyl chloroformate.

White crystals of the expected product, are obtained with a yield of 88%, the product having the following elemental analysis:

|            | C     | H    | N    | O     |
|------------|-------|------|------|-------|
| Calculated | 68.22 | 5.72 | 4.68 | 21.38 |
| Found      | 68.12 | 5.64 | 4.65 | 21.29 |

EXAMPLE 11

Preparation of 5,6-dihydroxy-1-(ethylthiocarbonyl)indoline

The reaction is carried out as shown in Example 2, except that 18.3 g (0.165M) of thioethyl chloroformate are added.

White crystals of the expected product are obtained with a yield of 77%, the product having the following elemental analysis:

|            | C     | H    | N    | O     | S     |
|------------|-------|------|------|-------|-------|
| Calculated | 55.21 | 5.48 | 5.85 | 20.06 | 13.40 |
| Found      | 55.25 | 5.46 | 5.79 | 20.29 | 13.18 |

DYEING EXAMPLES

EXAMPLE 1

The following compositions are prepared:

COMPOSITION (A)

| Copper sulfate pentahydrate | 1 g |
| Sodium lauryl ether sulfate, sold under the name "Empicol ESB/3 FL" by the Company Marchon | 4.2 g AM |

-continued

| | |
|---|---|
| Hydroxyethyl cellulose sold under the name "Cellosize WP 34" by the Company Union Carbide | 2.4 g AM |
| Monoethanolamine q.s. pH = 9.5 | |
| Water | q.s. for 100 g |

COMPOSITION (B)

| | |
|---|---|
| 5,6-Dihydroxy-1-(benzyloxycarbonyl)-indoline | 0.5 g |
| Dimethyl isosorbide | 15 g |
| Water | 10 g |
| Triethanolamine q.s. pH = 7.8 | |

The composition (A) is applied to natural gray hair containing 90% white hairs for 10 minutes and the hair is then rinsed. The solution (B) containing the indoline is then applied for 10 minutes. The hair is then rinsed and dried. The hair is colored in a golden ashy very light blonde shade.

EXAMPLE 2

The following compositions are prepared:

COMPOSITION (A)

| | |
|---|---|
| 5,6-Dihydroxy-1-(benzyloxycarbonyl)-indoline | 0.5 g |
| Dimethyl isosorbide | 15 g |
| Water | 10 g |
| Triethanolamine q.s. pH = 7.8 | |

COMPOSITION (B)

| | |
|---|---|
| Sodium metaperiodate | 5 g |
| Hydrochloric acid q.s. pH = 3 | |
| Water | q.s. for 100 g |

The composition (A) is applied to permanent wave gray hair containing 90% white hairs for 15 minutes and the hair is then rinsed. The composition (B) is then applied for 15 minutes. The hair is then rinsed and dried.

The hair is colored in a golden light blonde shade.

EXAMPLES 3 to 10

The following compositions are prepared:

COMPOSITION (A)

| | |
|---|---|
| Copper sulfate pentahydrate | 1 g |
| Sodium lauryl ether sulfate, sold under the name "Empicol ESB/3 FL" by the Company Marchon | 4.2 g AM |
| Hydroxyethyl cellulose sold under the name "Cellosize WP 34" by the Company Union Carbide | 2.4 g AM |
| Monoethanolamine q.s. pH = 9.5 | |
| Water | q.s. for 100 g |

COMPOSITION (B)

| | |
|---|---|
| Indoline of formula (I) | 0.5 g |
| Dimethyl isosorbide | 15 g |
| Water | 10 g |
| Triethanolamine q.s. pH = 7.8 | |

The composition (A) is applied for 10 minutes to natural or permanent wave gray hair containing 90% white hairs and the hair is then rinsed.

The composition (B) containing the indoline is then applied for 10 minutes. The hair is then rinsed and dried.

The colors obtained are shown in the table below:

TABLE

| EXAMPLES | INDOLINE | COLOR ON NATURAL GRAY HAIR CONTAINING 90% WHITE HAIRS | COLOR ON PERMANENT WAVE GRAY HAIR CONTAINING 90% WHITE HAIRS |
|---|---|---|---|
| 3 | 5,6-dihydroxy-1-(ethyloxycarbonyl)indoline | Matt golden ashy | |
| 4 | 5,6-dihydroxy-1-(isopropyloxycarbonyl)indoline | | Matt golden ashy |
| 5 | 5,6-dihydroxy-1-(allyloxycarbonyl)indoline | Matt golden ashy | |
| 6 | 5,6-dihydroxy-1-(2-ethylhexyloxycarbonyl)indoline | | Matt golden ashy |
| 7 | 5,6-dihydroxy-1-(2,2,2-trichloroethoxycarbonyl)indoline | Matt golden ashy | |
| 8 | 4-hydroxy-5-methoxy-1-(benzyloxycarbonyl)indoline | | Matt golden ashy |
| 9 | 6-hydroxy-7-methoxy-1-(benzyloxycarbonyl)indoline | Matt golden ashy | |
| 10 | 6,5-dihydroxy-1-(methoxyethoxycarbonyl)indoline | | Matt golden ashy |

EXAMPLES 11 TO 18

The following compositions are prepared:

COMPOSITION (A)

| | |
|---|---|
| Indoline of formula (I) | 0.5 g |
| Dimethyl isosorbide | 15 g |
| Water | 10 g |
| Triethanolamine q.s. pH = 7.8 | |

COMPOSITION (B)

| | |
|---|---|
| Sodium metaperiodate | 5 g |
| HCl q.s. pH = 3 | |
| Water | q.s. for 100 g |

The composition (A) is applied for 15 minutes to natural or permanent wave gray hair containing 90% white hairs and the hair is then rinsed. The composition (B) is then applied for 15 minutes. The hair is then rinsed and dried.

The colors obtained are shown in the table below.

TABLE

| EXAMPLES | INDOLINE | COLOR ON NATURAL GRAY HAIR CONTAINING 90% WHITE HAIRS | COLOR ON PERMANENT WAVE GRAY HAIR CONTAINING 90% WHITE HAIRS |
|---|---|---|---|
| 11 | 5,6-dihydroxy-1-(ethyloxycarbonyl)indoline | Golden beige | |
| 12 | 5,6-dihydroxy-1-(isopropyloxycarbonyl)indoline | | Golden beige |
| 13 | 5,6-dihydroxy-1-(allyloxycarbonyl)indoline | Golden beige | |

TABLE-continued

| EXAMPLES | INDOLINE | COLOR ON NATURAL GRAY HAIR CONTAINING 90% WHITE HAIRS | COLOR ON PERMANENT WAVE GRAY HAIR CONTAINING 90% WHITE HAIRS |
|---|---|---|---|
| 14 | 5,6-dihydroxy-1-(2-ethylhexyloxycarbonyl)-indoline | | Slightly iridescent golden beige |
| 15 | 5,6-dihydroxy-1-(2,2,2-trichloroethoxycarbonyl)indoline | Golden beige | |
| 16 | 4-hydroxy-5-methoxy-1-(benzyloxycarbonyl)-indoline | | Golden beige |
| 17 | 6-hydroxy-7-methoxy-1-(benzyloxycarbonyl)-indoline | Golden beige | |
| 18 | 6,5-dihydroxy-1-(methoxyethoxycarbonyl)indoline | | Golden beige |

We claim:

1. An indoline compound having the formula

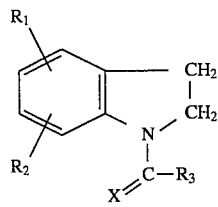

(I)

wherein $R_1$ and $R_2$, each independently, represent hydrogen, $C_1-C_4$ alkyl, $C_1-C_4$ monohydroxyalkyl, $C_2-C_4$ polyhydroxyalkyl, hydroxyl, $C_1-C_4$ alkoxy or NHR wherein R represents hydrogen, $C_1-C_4$ alkyl, $C_1-C_4$ monohydroxyalkyl or $C_2-C_4$ polyhydroxyalkyl;

X represents an oxygen atom or a sulfur atom;

$R_3$ represents —$OR_4$ or $NR_5R_6$;

$R_4$ represents a linear or branched $C_1-C_{10}$ alkyl, a linear or branched $C_2-C_{10}$ alkenyl, benzyl, alkoxyalkyl wherein the alkyl and alkoxy moieties have 1–4 carbon atoms or $C_1-C_4$ haloalkyl;

$R_5$ and $R_6$, each independently, represent $C_1-C_4$ alkyl;

with the proviso that $R_1$ and $R_2$ do not simultaneously represent hydrogen and when $R_1$ represents alkyl, alkoxy, mono- or polyhydroxyalkyl, $R_2$ represents hydroxyl or NHR wherein R has the meaning given above; with the exception of 5-amino-1-(N,N-dimethylcarbamoyl)indoline.

2. The compound of claim 1 selected from the group consisting of:

5,6-dihydroxy-1-(benzyloxycarbonyl)indoline,
5,6-dihydroxy-1-(ethyloxycarbonyl)indoline,
5,6-dihydroxy-1-(isopropyloxycarbonyl)indoline,
5,6-dihydroxy-1-(allyloxycarbonyl)indoline,
5,6-dihydroxy-1-(2,2,2-trichloroethoxycarbonyl)indoline,
5,6-dihydroxy-1-(2-ethylhexyloxycarbonyl)indoline,
5,6-dihydroxy-1-(methoxyethoxycarbonyl)indoline,
5,6-dihydroxy-1-(dimethylcarbamoyl)indoline,
4-hydroxy-5-methoxy-1-(benzyloxycarbonyl)indoline,
6-hydroxy-7-methoxy-1-(benzyloxycarbonyl)indoline,
5-methoxy-6-hydroxy-1-(benzyloxycarbonyl)indoline.

* * * * *